(12) United States Patent
Yee

(10) Patent No.: US 6,669,661 B1
(45) Date of Patent: Dec. 30, 2003

(54) METHOD AND DEVICE FOR CENTRAL NERVOUS SYSTEM PROTECTION DURING WHOLE BODY HYPERTHERMIA OR HYPOTHERMIA

(76) Inventor: Thomas C. Yee, 2330 Paseo Del Prado, Suite 20, Las Vegas, NV (US) 89102

( * ) Notice: Subject to any disclaimer, the term of this patent is extended or adjusted under 35 U.S.C. 154(b) by 0 days.

(21) Appl. No.: 09/538,928

(22) Filed: Mar. 30, 2000

Related U.S. Application Data

(63) Continuation-in-part of application No. 08/938,470, filed on Sep. 29, 1997, now abandoned.

(51) Int. Cl.⁷ .................. A61M 37/00; A61M 1/00; A61M 1/36; A61H 21/00; A61C 7/00
(52) U.S. Cl. ............. 604/6.13; 604/4.01; 604/6.16; 604/28; 422/45; 607/87; 607/104
(58) Field of Search .............. 422/44–48; 604/4.01, 604/5.01–5.04, 6.08, 6.09, 6.11, 6.13, 6.14, 6.16, 19, 27, 28, 8–9, 30, 31, 500, 507–509, 513, 65–67, 96.01, 101.01, 101.03–101.04, 104, 113, 114, 131, 151, 264, 523, 532; 210/645–47, 650–51, 739, 742–43, 348, 416.1; 128/200.29, 898, DIG. 3; 601/3; 606/191–92, 198, 194–95; 607/1–3, 81, 85–87, 104–106, 108–111; 435/1.1, 1.2, 1.3, 283.1, 284.1, 297.1–297.4, 286.5; 4/488, 493, 496, 498, 507, 509, 661, 538–39, 545, 553; 5/1, 11, 613–14, 600, 606–607, 611–12, 421, 900; D24/201–205; 514/816–818

(56) References Cited

U.S. PATENT DOCUMENTS

| | | | | |
|---|---|---|---|---|
| 4,904,237 A | * | 2/1990 | Janese | 604/28 |
| 5,354,277 A | * | 10/1994 | Guzman et al. | 604/113 |
| 5,476,444 A | * | 12/1995 | Keeling et al. | 604/6.13 |
| 5,713,941 A | * | 2/1998 | Robins et al. | 607/96 |
| 5,730,720 A | * | 3/1998 | Sites et al. | 604/27 |
| 5,741,317 A | * | 4/1998 | Ostrow | 607/85 |
| 5,820,593 A | * | 10/1998 | Safar et al. | 604/96.01 |
| 5,837,003 A | * | 11/1998 | Ginsburg | 607/106 |
| 6,110,139 A | * | 8/2000 | Loubser | 604/30 |
| 6,516,224 B2 | * | 2/2003 | Lasersohn et al. | 607/3 |

* cited by examiner

Primary Examiner—Patricia Bianco
(74) Attorney, Agent, or Firm—Robert Ryan Morishita; Anderson & Morishita, LLC

(57) ABSTRACT

A method and device for intentionally inducing whole-body hyperthermia or hypothermia in a patient for medical treatment while protecting the central nervous system from damage includes a tub for immersing the patient's body in a solution with a temperature greater than or less than normal body temperature to thereby increase or decrease the patient's body temperature. The patient's cerebral spinal fluid is circulated and maintained at temperatures less drastically altered from normal temperatures by a pump and a heater and cooler connected to the patient's spine through catheters. The patient's central nervous system blood is separated from the rest of the circulatory system and circulated and maintained at temperatures less drastically altered from normal temperatures by pumps and a heater and cooler. The remaining blood in the patient's body is circulated and temperature controlled through pumps and a heater and cooler.

18 Claims, 3 Drawing Sheets

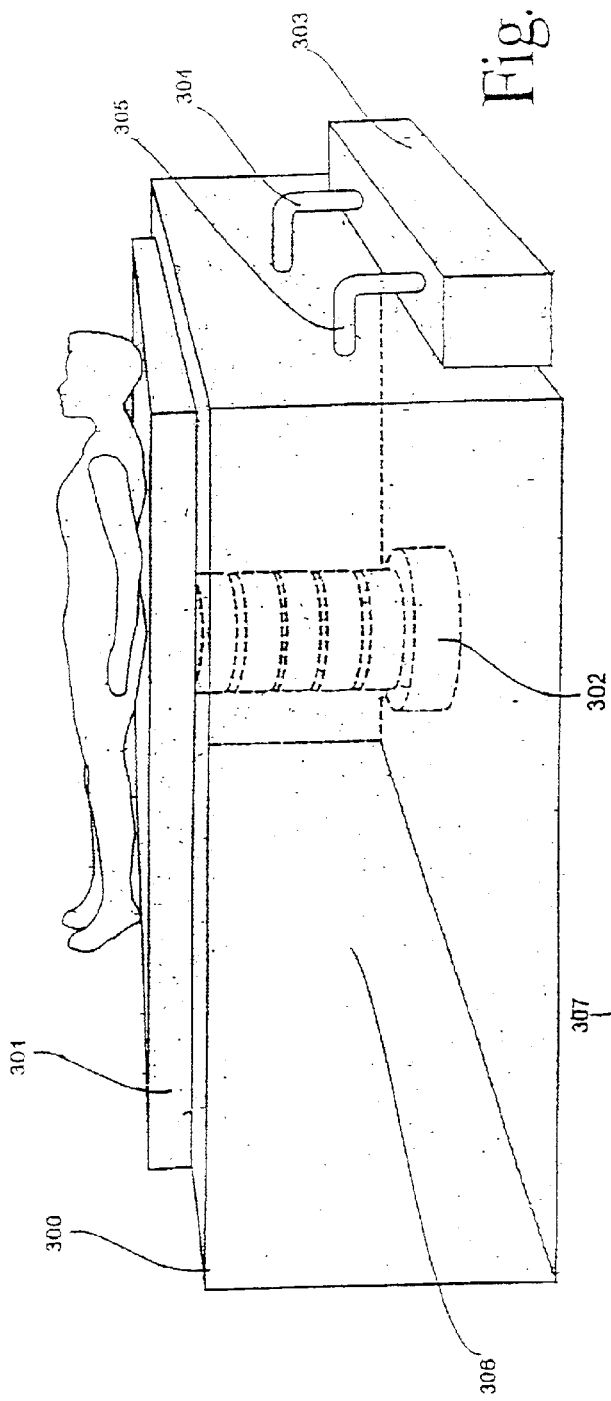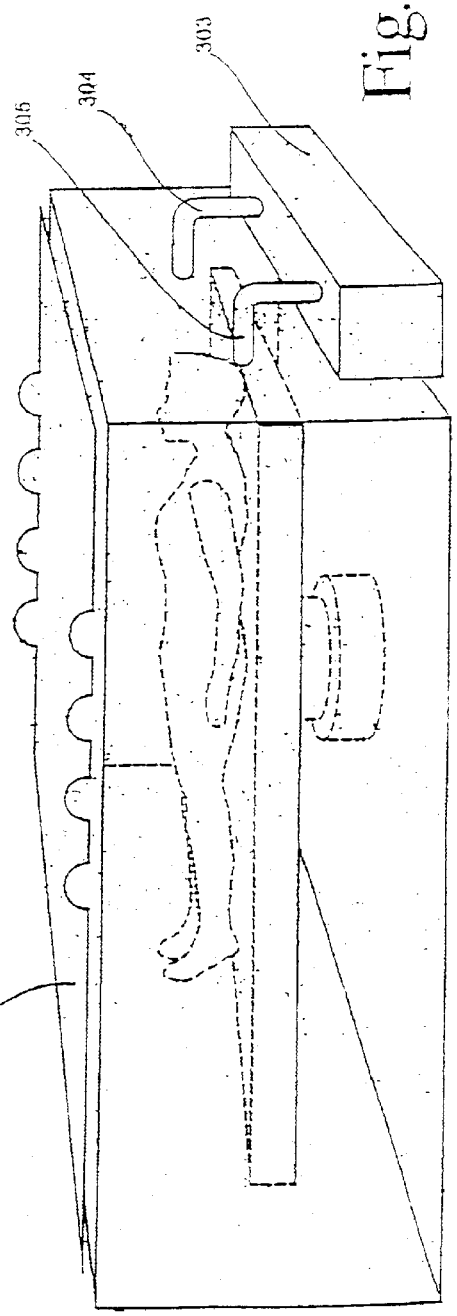

US 6,669,661 B1

METHOD AND DEVICE FOR CENTRAL NERVOUS SYSTEM PROTECTION DURING WHOLE BODY HYPERTHERMIA OR HYPOTHERMIA

RELATED APPLICATION DATA

This application is a continuation-in-part of U.S. patent application Ser. No. 08/938,470 filed Sep. 29, 1997, now abandoned.

FIELD OF THE INVENTION

The present invention relates to intentionally induced hypo- or hyperthermia medical treatments. Specifically, the present invention is a method and device for inducing whole-body hypo- or hyperthermia while protecting the central nervous system to prevent neurological damage during the hypo- or hyperthermia procedure.

BACKGROUND OF THE INVENTION

The normal body temperature in a human varies depending on a variety of factors but typically ranges between 36.1° C. and 37.2° C. The factors which may influence a person's body temperature include physical activity, environmental conditions, and even the time of day.

It is also well known that an increase in body temperature is a normal response to a bacterial or viral infection. This change in body temperature occurs because bacteria and viruses cannot survive outside a fairly narrow range of temperatures. Likewise, it is known that cancer cells, HIV (human immunodeficiency virus), and hepatitis virus cannot survive extreme temperatures.

To take advantage of this susceptibility to temperature extremes, it is well accepted in the art that intentionally induced single limb hyperthermia is an acceptable treatment for cancer isolated in limbs. However, it is also known in the art that whole body hyperthermia can cause serious side effects such as increased acidity in the blood and neurological damage. Thus, intentionally induced whole-body hyperthermia has not been feasible to treat cancers which are not isolated in limbs.

For the same reason, intentionally induced whole-body hyperthermia has not been a feasible treatment for bacterial or viral infection. For example, Ginsburg, U.S. Pat. No. 5,486,208, discloses a method and apparatus for controlling a patient's body temperature by transferring heat to a patient's blood via a catheter. However, Ginsburg does not address the possible neurological damage that could be caused by the increase in body temperature.

Similarly, Keeling, U.S. Pat. No. 5,476,444 discloses a method for increasing the temperature of the blood extracorporeally. However, by not increasing the temperature of the body itself above 45° C., the method of Keeling does not raise the body temperature to a level high enough to kill the viruses, bacteria, or cancer cells. Moreover, like Ginsburg, the method of Keeling does not disclose a method for protecting the central nervous system from neurological damage caused by the increased body temperature.

It is also known in the art that it is desirable to intentionally induce hypothermia for treatment purposes. For example, during cardiac surgery, the body temperature may be reduced to between 18° C. and 20° C. to allow complete circulatory arrest. However, it is well known that such hypothermia must usually be limited to less than sixty minutes to prevent neurological damage.

Thus, it can be seen that there is a need in the art for a method and device for raising the body temperature above 45° C. or lowering the body temperature below 20° C. for extended periods of time to allow medical treatment without risking neurological damage.

SUMMARY OF THE INVENTION

The present invention, a device for intentionally inducing whole-body hyperthermia or hypothermia in a patient while protecting the central nervous system, has four major components. First, the invention includes a tub for immersing the patient's body in a solution with a temperature greater than or less than normal body temperature to increase or decrease the patient's body temperature.

Second, the invention includes a system for circulating the patient's cerebral spinal fluid. The circulator includes a catheter inserted into the patient's spinal canal and a pump to withdraw the patient's cerebral spinal fluid. A heater and cooler control the temperature of the cerebral spinal fluid and a fluid port allows a medical professional to alter the chemical characteristics of the cerebral spinal fluid. Preferably, a thermocouple is provided to automatically control the temperature of the cerebral spinal fluid. In a preferred embodiment, anesthetic is introduced into the cerebral spinal fluid through the fluid port to induce a profound nerve blockade and a calcium-channel blocker and membrane stabilizing agents are introduced to reduce injury to the central nervous system tissues during treatment. A pump reintroduces the cerebral spinal fluid into the patient through a catheter inserted into the patient's spinal canal.

Third, the invention includes a system for circulating the patient's central nervous system blood. The central nervous system blood circulator includes input catheters inserted into the patient's right and left jugular veins and output catheters inserted into the patient's right and left vertebral arteries and right and left carotid arteries. A pump withdraws the blood from the patient's central nervous system through the input catheters. A hemodialysis device known in the art controls the chemical characteristics of the withdrawn central nervous system blood and a heater and cooler control the temperature of the withdrawn central nervous system blood. A membrane exchanger known in the art oxygenates the central nervous system blood. The central nervous system blood is passed through a filter to remove blood clots. The pump reintroduces the central nervous system blood into the patient. Preferably, a thermocouple is provided to automatically control the temperature of the central nervous system blood. In a preferred embodiment, anesthetic is introduced into the central nervous system blood through a fluid port to induce a nerve blockade and a calcium-channel blocker and membrane stabilizing agents are introduced to reduce damage to the central nervous system tissues during treatment.

Fourth, the invention includes a device for circulating the blood through the remainder of the patient's circulatory system. The body blood circulator includes an input catheter inserted into the patient's femoral vein and an output catheters inserted into the patient's femoral arteries. A pump withdraws the blood from the patient's body through the input catheter. A hemodialysis device known in the art controls the chemical characteristics of the withdrawn body blood and a heater and cooler control the temperature of the withdrawn body blood. A membrane exchanger known in the art oxygenates the body blood. The body blood is passed through a filter to remove blood clots. The pump reintroduces the body blood into the patient. Preferably, a thermocouple is provided to automatically control the temperature of the body blood. In a preferred embodiment, anesthetic is introduced into the body blood through a fluid port to anesthetize the patient and induce a nerve blockade and a calcium-channel blocker and membrane stabilizing agents are introduced to reduce damage and injury to the tissues during treatment.

In use, the patient is first anesthetized. The cerebral spinal fluid circulator is connected to the patient's spinal canal and the central nervous system blood circulator and body blood circulator are connected to the patient's circulatory system as described above. The cerebral spinal fluid, central nervous system blood, and body blood are circulated and treated as described above. The patient is then immersed in a solution to raise or lower the body temperature. Preferably, the cerebral spinal fluid and central nervous system blood are maintained at a desired target temperature for treatment. The induced whole-body hypothermia or hyperthermia is maintained for a predetermined period of time. The temperature of the solution is then gradually changed to near normal body temperature.

It is an object of the present invention to provide a method and device for inducing hypothermia or hyperthermia while protecting the central nervous system from damage caused by extreme temperatures.

BRIEF DESCRIPTION OF THE DRAWINGS

FIG. 3 is a schematic drawing of the tub of the present invention with a patient on the platform;

FIG. 4 is a schematic drawing of the tub of the present invention with a patient on the platform lowered into the tub and immersed in the saline solution.

DESCRIPTION

Figure 1:
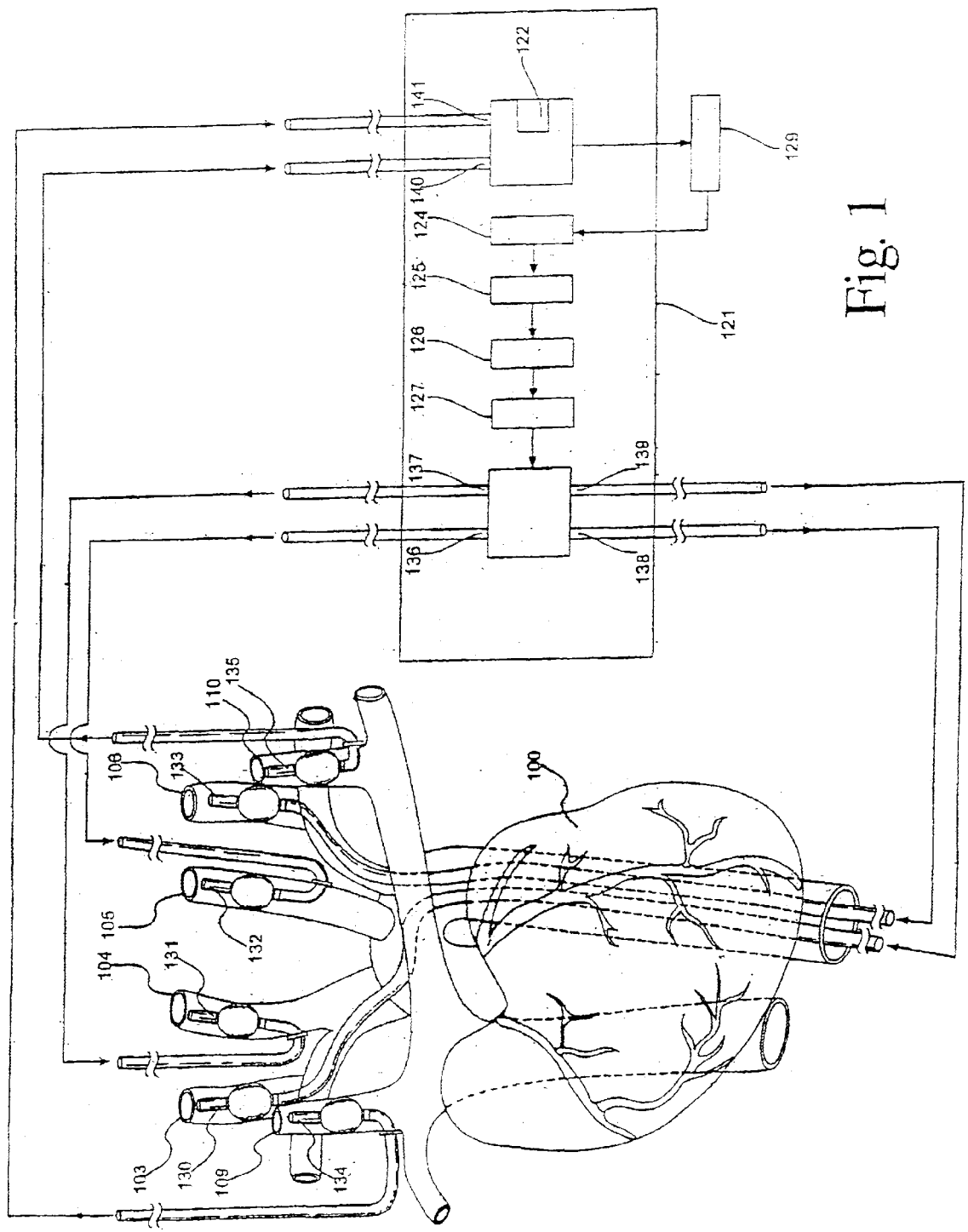
FIG. 1 is a schematic drawing of the central nervous system blood circulator of the present invention.
Figure 2:
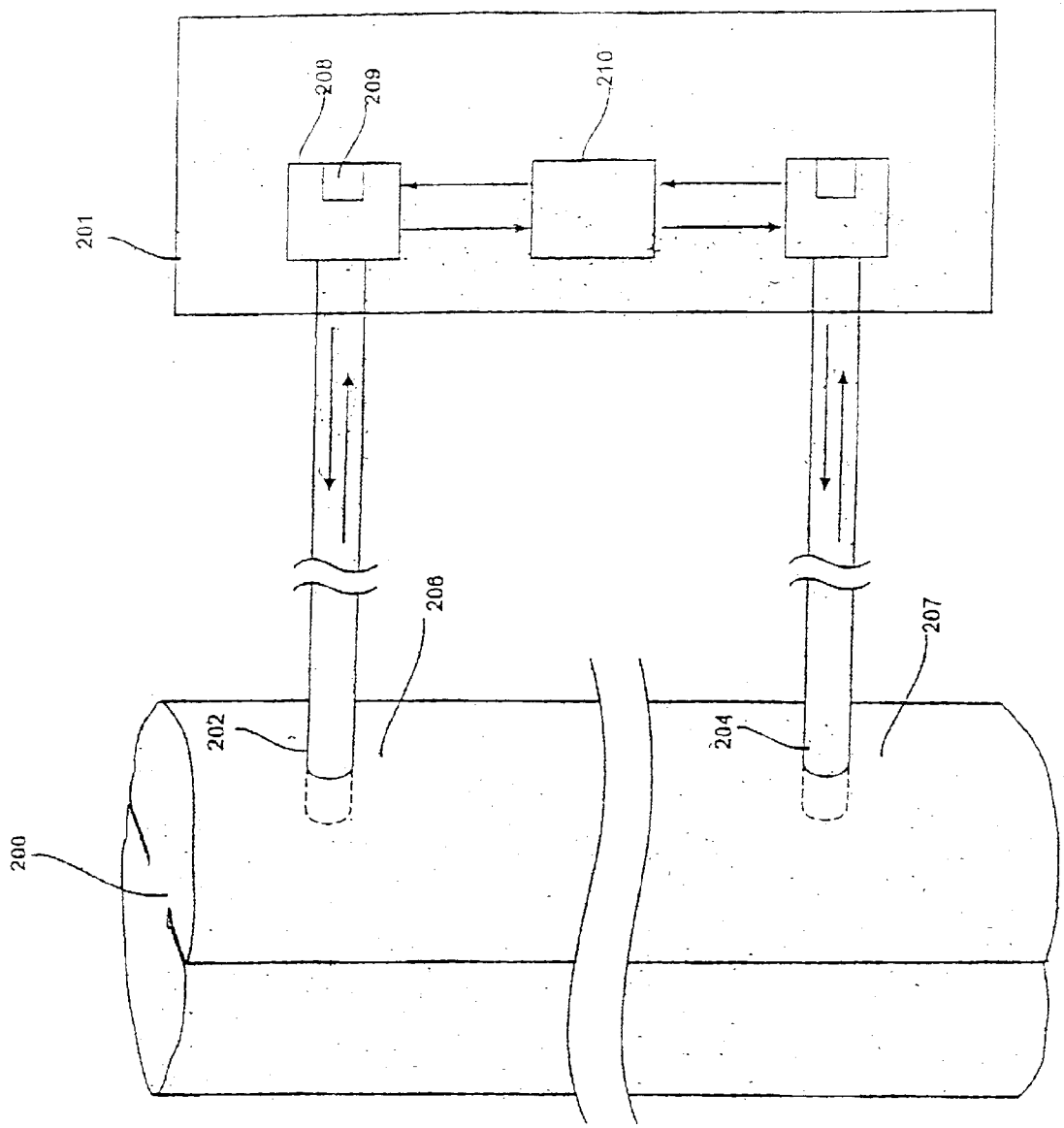
FIG. 2 is a schematic drawing of the cerebral spinal fluid circulator.

Reference is now made to the figures wherein like parts are referred to by like numerals throughout. With reference to FIGS. 1 and 2, because it is known that the central nervous system can suffer permanent damage as a result of extreme temperatures, the present invention also includes a central nervous system ("CNS") blood circulator 121 and a cerebral spinal fluid ("CSF") circulator. The CNS blood circulator 121 and CSF circulator 201 are intended to control temperature of the blood and spinal fluid flowing to the central nervous system independent of the body temperature. Thus, even through the body temperature may reach over 48° C., a temperature that is normally not survivable, during use of the present invention, permanent neurological damage is avoided because the central nervous system is maintained at a more moderate temperature by use of the CNS blood circulator 121 and the CSF circulator 201. Simultaneously, however, the temperature of the CNS blood and CSF is elevated above normal or reduced below normal to effectively treat the viral or bacterial infection.

More specifically, FIG. 1 shows the preferred embodiment of the CNS blood circulator 121. The CNS blood circulator 121 includes six balloon-cuff-tipped catheters 130–135. Two of the catheters are designated input catheters 134, 135 and are inserted into the patient's left jugular vein 110 and right jugular vein 109. These input catheters 134, 135 are fluidly connected to the intakes 140, 141 of a CNS blood pump 125.

The four remaining catheters are designated output catheters 130–133 and are inserted into the patient's left carotid artery 105, right carotid artery 104, right vertebral artery 103, and left vertebral artery 106. These output catheters 130–133 are fluidly connected to the outputs 136–139 of the CNS blood pump 125.

The CNS blood pump 125 is fluidly connected to a heater and cooler 126 for controlling the temperature of the CNS blood. Preferably, the heater and cooler are controlled by a thermocouple (not shown). The CNS blood pump 125 is fluidly connected to a hemodialysis device 129 known in the art to control the chemical characteristics, such removing metabolites and waste products from the CNS blood. Downstream of the hemodialysis device 129 is a membrane oxygenator 124 known in the art to oxygenate the blood and remove carbon dioxide. The membrane oxygenator 124 fluidly communicates with a filter 127 for removing blood clots and air bubbles and a port 122 for sampling the CNS blood and adding fluids to the blood.

The CSF circulator 201 includes two catheters 202, 204 which are inserted into the subarachnoid space in a patient's spine 200. The intake catheter 202 is connected to the intake of a CSF pump 208 which draws the CSF from the spine 200. A heater and cooler 210 controls the temperature of the CSF and the CSF is returned to the spine though the outlet catheter 204. A port 209 may be provided for sampling the CSF and injecting fluids into the CSF. In a preferred embodiment, one catheter is inserted into the cervical thoracic region 206 and the other is inserted into the lumbar region 207.

With reference to FIG. 3, the present invention includes a tub 300 containing a saline solution 306 underneath a movable platform 301. A flexible cover 307 may be provided to prevent undesired heat loss or gain. The tub 300 is preferably of a size to allow a patient to be fully immersed. The tub 300 is preferably filled with a physiologic saline 306 with a salinity matching normal human blood serum. The saline 306 may also include antibiotics to prevent bacterial growth. An external pump, heater, cooler, thermocouple are contained in a housing 303. The pump circulates the saline 306 and the heater, cooler, and thermocouple control the temperature of the saline 306 through pipes 304, 305.

In the method of the present invention, a patient is positioned on the platform 301 of the device. Monitors, including a blood pressure monitor, pulse oximeter probe, electrocardiogram, skin temperature sensor, electroencephalogram, and sensory evoked potential monitor are connected to the patient.

General anesthetic, such as Pentothal®, propofol, or the like, is administered to the patient. In an optional embodiment, the general anesthetic is administered by adding the general anesthetic directly to the cerebral spinal fluid to thereby reduce the activity of the brain cells. This results in a reduction in the oxygen requirements of the brain cells. As the general anesthetic takes effect, an endotracheal intubation is performed to allow ventilation of the patient.

Local anesthetic, such as lidocaine Marcaine®, or the like, is injected into the patient to induce paralysis and arrest breathing and heart activity. For example, the local anesthetic could be administered by injecting the local anesthetic into the spinal canal between the T1 and T4 vertebrae, thereby intentionally inducing a high spinal or total spinal. The local anesthetic may optionally be a sodium channel and/or potassium channel blocker to reduce or cease nerve activity.

Invasive monitors such as an arterial line in the radial artery, central venous intravenous line in the subclavian vein, esophageal echo cardiography probe in the esophagus, temperature sensors in the rectum, urinary bladder, and ear canal. A pulmonary artery catheter with internal cardiac pacing capability may be inserted via the subclavian venous central line into the right side of the heart 100. A foley urinary bladder catheter may be placed through the urethra into the bladder and external cardiac pacer lead pads may be placed on the patient's anterior chest and back.

Large bore catheters are inserted into the patient's femoral vein and femoral artery. These catheters will allow a pump to circulate the blood excluding the CNS blood during the procedure. A hemodialysis machine and membrane oxygenator clean and oxygenate this body blood. Because this body blood does not reach the CNS, this blood can also be heated or cooled using a heater or cooler as part of the treatment. In other words, this blood may be drastically altered from normal body temperatures because it will be separated from the CNS blood by the CNS balloon catheters 130–135. In short, the novel approach of the present invention is to separate the circulatory system into a CNS blood system in which the blood temperature is maintained at a less drastically altered temperature and a body blood system which can be more aggressively thermally manipulated. Although less drastic temperature ranges could be used, in an optional embodiment, the body blood may be raised to a temperature above 45° C. or lowered to a temperature below 20° C. The temperature range of the CNS blood and the CSF is less drastic; an optional range is between 18° C. to 43° C.

Each of the CNS balloon catheters 130–135 are inserted into the patient and positioned as described above. The balloon catheters 130–135 are inflated to separate the CNS blood from the rest of the patient's circulatory system. The CNS blood circulator 121 is activated and the CNS blood is treated as described above. The temperature of the CNS blood is maintained at a temperature less severely altered from the body temperature such as between 18° C. to 43° C. In a preferred embodiment, the blood pH level is also tested and maintained at a near normal level of 7.40. Preferably, a general anesthetic is injected into the CNS blood through the port 122. Also, a calcium-channel blocker and membrane stabilizing agent are injected through the port 122 as well to stop conduction of the nerves and prevent degradation of the neurologic tissue during treatment.

The CSF circulator 201 is connected to the patient's spine as described above. The CSF circulator 201 is activated and the CSF is treated as described above. Like the CNS blood, the CSF is maintained at a temperature less drastically altered from the normal body temperature. In an optional embodiment, a range between 18° C. and 43° C. may be used. Also, the CSF is preferably maintained at a near normal pH level. In an optional embodiment, a calcium channel blocker is injected into the CSF to mediate cell degradation and cell destruction and a membrane stabilizing agent is injected into the CSF to reduce brain and nervous system activity. Optionally the membrane stabilizing agents may be beta blockers, that is, agents to block beta receptors. Also, in an optional embodiment, central nervous system inhibitors, such as valium, haldol, or the like, may be introduced into the CSF to reduce nervous system and brain activity.

The patient is lowered into the tub 300 and immersed in the saline solution 306. The patient's body temperature is raised or lowered as required by the procedure by increasing or decreasing the temperature of the saline solution and by controlling the temperature of the body blood. To a less drastic extent, the temperature of the CSF and the CNS blood is also altered and controlled. While the temperature increase or decrease rate could vary from patient to patient, in a preferred embodiment, the patient's temperature is increased or decreased between 1° C. and 2° C. every five minutes.

In hyperthermia therapy, cardiac dysrhythmia and, consequently, cardiac arrest takes place at approximately 44° C. or higher. In hypothermia therapy, cardiac dysrhythmia and, consequently, cardiac arrest takes place at approximately 28° C. or lower. When arrhythmia occurs, cardioplegic solution is injected into the central venous intravenous vein catheter to stop the contraction and electrical activity of the heart 100.

The duration of the hypo- or hyperthermia treatment differs depending on the particular reason for the treatment. After the predetermined time has elapsed, the patient's body temperature is gradually returned to near normal temperature using the saline solution, body blood, CNS blood, and CSF. The return temperature rate is approximately 1° C. per five minutes.

When the patient's body temperature nears normal temperature, the patient is raised out of the saline solution 306 in the tub 300 using the lift shaft 302. The blood chemistries are returned to normal levels using techniques known in the art. The heart 100 will return to normal function either on its own once the potassium levels are reduced to normal levels or by use of a defibrillator and cardiac pacemaker via either the internal or external pacer. When the cardiac output approaches normal levels of 2.5 liters per minute, the body blood pump is deactivated. The CNS blood circulator 121 and the CSF circulator 201 are deactivated to allow the CNS to resume normal function.

Anesthesia is ceased and the patient is allowed to return to consciousness. The endotracial tube is removed and the CNS circulator 121 and the CSF circulator 201 are removed.

An advantage of the present invention is that the benefits of induced hyperthermia or hypothermia treatment may be realized without damage to the brain and other neurologic structures because the central nervous system is maintained at a less severely altered temperature by controlling the temperature of the central nervous system blood and cerebral spinal fluid and by introduction of various anesthetic agents, calcium channel blockers, and membrane stabilizing agents directly into CNS blood and CSF.

I claim:

1. A method for intentionally inducing whole-body hyperthermia or hypothermia while protecting the central nervous system in a patient for medical treatment, comprising:

immersing the patient in a fluid bath with a temperature greater than or less than normal body temperature to thereby increase or decrease the patient's body temperature;

circulating the patient's cerebral spinal fluid comprising steps of:

withdrawing the patient's cerebral spinal fluid;

introducing a membrane stabilizing agent into the cerebral spinal fluid;

controlling the temperature and chemical characteristics of the withdrawn cerebral spinal fluid, reintroducing the cerebral spinal fluid into the patient;

circulating the patient's central nervous system blood comprising steps of:

withdrawing the blood from the patient's central nervous system;

controlling the temperature and chemical characteristics of the withdrawn central nervous system blood;

oxygenating the central nervous system blood, and reintroduces the central nervous system blood into the patient;

circulating the remaining blood in the patient's body comprising steps of:

withdrawing the blood from the remainder of the patient's body;

controlling the temperature and chemical characteristics of the withdrawn body blood;

oxygenating the body blood; and reintroducing the body blood into the patient; and returning the patient's body temperature to a normal level after a predetermined time.

2. The method of claim 1 further comprising introducing a calcium-channel blocker into the cerebral spinal fluid.

3. The method of claim 1 further comprising introducing a calcium-channel blocker into the central nervous system blood.

4. The method of claim 1 further comprising introducing a calcium-channel blocker into the body blood.

5. The method of claim 1 further comprising introducing a general anesthetic into the cerebral spinal fluid.

6. The method of claim 1 further comprising introducing a general anesthetic into the central nervous system blood.

7. The method of claim 1 further comprising introducing a general anesthetic into the body blood.

8. The method of claim 1 further comprising introducing a local anesthetic into the cerebral spinal fluid.

9. The method of claim 8 wherein the local anesthetic is a potassium-channel blocker.

10. The method of claim 8 wherein the local anesthetic is a sodium-channel blocker.

11. The method of claim 1 further comprising introducing a local anesthetic into the central nervous system blood.

12. The method of claim 11 wherein the local anesthetic is a potassium-channel blocker.

13. The method of claim 11 wherein the local anesthetic is a sodium-channel blocker.

14. The method of claim 1 further comprising introducing a local anesthetic into the body blood.

15. The method of claim 14 wherein the local anesthetic is a potassium-channel blocker.

16. The method of claim 14 wherein the local anesthetic is a sodium-channel blocker.

17. The method of claim 1 wherein the membrane stabilizing agent is a beta blocker.

18. The method of claim 1 further comprising introducing a central nervous system inhibitor into the cerebral spinal fluid.

* * * * *